(12) United States Patent
Barrett-Reis et al.

(10) Patent No.: US 7,829,126 B2
(45) Date of Patent: Nov. 9, 2010

(54) INFANT FORMULAS CONTAINING DOCOSAHEXAENOIC ACID AND LUTEIN

(75) Inventors: Bridget Barrett-Reis, Dublin, OH (US); Pamela T. Price, Granville, OH (US); Amy Mackey, Columbus, OH (US)

(73) Assignee: Abbott Laboratories, Abbott Park, IL (US)

( * ) Notice: Subject to any disclaimer, the term of this patent is extended or adjusted under 35 U.S.C. 154(b) by 632 days.

(21) Appl. No.: 11/584,704

(22) Filed: Oct. 20, 2006

(65) Prior Publication Data

US 2007/0098849 A1    May 3, 2007

Related U.S. Application Data

(60) Provisional application No. 60/730,283, filed on Oct. 26, 2005.

(51) Int. Cl.
     *A61K 38/01*      (2006.01)

(52) U.S. Cl. ............... 426/72; 514/2; 514/21; 426/658; 426/800; 426/801; 424/655; 424/442; 424/600

(58) Field of Classification Search ............ 426/72
See application file for complete search history.

(56) References Cited

U.S. PATENT DOCUMENTS

| | | |
|---|---|---|
| 5,550,156 A | 8/1996 | Kyle |
| 6,649,195 B1 | 11/2003 | Gorsek |
| 7,090,862 B2 | 8/2006 | Barrett-Reis et al. |
| 7,090,879 B2 | 8/2006 | Albrecht et al. |
| 2003/0228392 A1* | 12/2003 | Zimmer ............ 426/73 |
| 2005/0106272 A1 | 5/2005 | Lang et al. |
| 2005/0208179 A1* | 9/2005 | Albrecht et al. ........ 426/72 |
| 2006/0088574 A1 | 4/2006 | Manning et al. |
| 2006/0270739 A1 | 11/2006 | Johnson et al. |

FOREIGN PATENT DOCUMENTS

| | | |
|---|---|---|
| FR | 2882894 | 9/2006 |
| WO | WO02/200208 A2 | 3/2002 |
| WO | WO2005/009422 A1 | 2/2005 |
| WO | WO2005/087208 A2 | 9/2005 |
| WO | WO2005/110375 A1 | 11/2005 |
| WO | WO2006/116755 A2 | 11/2006 |

OTHER PUBLICATIONS

Cantrill, Richard, 'Lutein from Tagetes Erecta', FAO, 2004, <ftp://ftp.fao.org/es/esn/jecfa/cta/CTA_63_Lutein.pdf>.*
Greene, Alan, 'How Much Milk Should Baby Be Drinking?', published Jan. 2001.*
Snodderly, et al., "The Influence of Supplemental Lutein and Docosahexaenoic Acid on Their Serum Levels and on Macular Pigment", Investigative Ophthalmology & Visual Science, 2005, vol. 46, E-Abstract 1766.
International Search Report and Written Opinion from PCT/US2006/041303, dated Jun. 12, 2007.
Carlson, et al., "Visual-acuity Development in Healthy Preterm Infants: Effect of Marine-Oil Supplementation," American Journal of Clinical Nutrition, vol. 58, No. 1, p. 35-42 (1993).
Written Opinion from Singapore application No. 200802192-5, dated May 7, 2009.

* cited by examiner

*Primary Examiner*—Jennifer C McNeil
*Assistant Examiner*—Hong Mehta
(74) *Attorney, Agent, or Firm*—Sandra E. Weida; William J. Winter (57) ABSTRACT

Disclosed are infant formulas and corresponding methods of using them to promote retinal health and vision development in infants. The formulas, which are free of egg phospholipids and comprise fat, protein, carbohydrate, vitamins, and minerals, including docosahexaenoic acid and, on a ready-to-feed basis, at least about 50 mcg/liter of lutein, wherein the weight ratio of lutein (mcg) to docosahexaenoic acid (mg) is from about 1:2 to about 10:1. The formulas are also believed to be especially useful in reducing the risk of retinopathy of prematurity in preterm infants.

17 Claims, 2 Drawing Sheets

INFANT FORMULAS CONTAINING DOCOSAHEXAENOIC ACID AND LUTEIN

This application claims the benefit of U.S. Provisional Application No. 60/730,283 filed Oct. 26, 2005

TECHNICAL FIELD

The present invention relates to infant formulas containing select combinations of docosahexaenoic acid and lutein for promoting retinal health and vision development in infants.

BACKGROUND OF THE INVENTION

Infant formulas are commonly used today to provide supplemental or sole source nutrition early in life. These formulas contain protein, carbohydrate, fat, vitamins, minerals, and other nutrients. They are commercially available as powders, ready-to-feed liquids, and liquid concentrates.

Although many infant formulas provide a quality alternative to human milk, they still do not provide the same high level of nutrition as found in human milk. As such, much of the research effort into infant formulas over the past several years has been directed to better understanding the natural constituents of human milk, and then modifying infant formulas accordingly, or at least to the extent possible with currently available technology.

Arachidonic acid and docosahexaenoic acid, for example, have been identified in human milk and subsequently added to synthetic infant formulas. These fatty acids support brain and vision development in infants, and are now commonly found in commercially available formulas such as Similac® Advance® Infant Formula, Isomil® Advance® Infant formula, and Similac® Special Care® Advance® infant formula, all of which are available from Ross Products Division, Abbott Laboratories, Columbus, Ohio, USA.

Lutein has also been identified in human milk. Although it is not currently added to infant formulas as an isolated ingredient, lutein can be found at low concentrations in infant formulas as an inherent ingredient in some of the natural oils commonly used make such formulas. Lutein is an antioxidant that also happens to concentrate within the retina of the eye. It is generally known that dietary lutein may provide individuals with eye health benefits, and it is speculated that such benefits may be extended to infants receiving lutein from either human milk or supplemented infant formula.

It is now believed that a combination of lutein and docosahexaenoic acid may be particularly important in promoting retinal health and vision development in infants. Both materials are present in human milk and both are known to concentrate in the retina in otherwise healthy subjects. Docosahexaenoic acid (DHA), as a polyunsaturated fatty acid, is highly susceptible to damage by oxidation and degradation within the eye, while lutein is a known antioxidant. It is believed that by adding lutein to infant formulas, not only will it concentrate within the retina, it may also reduce oxidative degradation of the retinal DHA and thus further promote retinal health and vision development in the infant.

It has now been found, however, that lutein concentrations in infant formula must be much higher than the lutein concentrations found in human milk in order to achieve the same plasma lutein concentrations found in breast fed infants due to a lower relative bioavailability of lutein from infant formula. Although infant formulas today typically contain less than about 20 mcg/liter of lutein, most of which comes inherently from added fats and oils, it has now been found that such lutein concentrations must exceed about 50 mcg/liter, preferably from about 100 mcg/liter to about 200 mcg/liter, in order to duplicate plasma lutein concentrations found in exclusively in breast fed infants.

Consequently, it has also been found that infant formulas containing combinations of lutein and DHA, as described above, should now be formulated with higher ratios (lutein to DHA) than are commonly found in human milk. These weight ratios of lutein (mcg) to DHA (mg) should now range from about 1:2 to about 10:1.

SUMMARY OF THE INVENTION

The present invention is directed to infant formulas comprising fat, protein, carbohydrate, vitamins, and minerals, including docosahexaenoic acid and at least about 50 mcg/liter of lutein, wherein the weight ratio of lutein (mcg) to docosahexaenoic acid (mg) is from about 1:2 to about 10:1. The present invention is also directed to methods of using the formulas to promote retinal health and vision development in infants, including reducing the risk of retinopathy of prematurity in infants, and protecting against the damaging effects of excessive natural or artificial light on the infants' eyes.

It has been found that infant formulas should be prepared with lutein concentrations of at least 50 mcg/liter if they are to produce the same plasma lutein concentrations found in breast fed infants, even though human milk itself typically contains no more than about 30 mcg/liter of lutein. It has also been found, consequently, that the weight ratio of lutein (mcg) to DHA (mg) in the infant formula should range from about 1:2 to about 10:1. It is believed that the combination of lutein and docosahexaenoic acid are particularly useful in promoting retinal health and vision development in infants, provided that sufficient quantities of each are designed into the infant formula as described herein.

DETAILED DESCRIPTION OF THE INVENTION

The infant formulas of the present invention comprise fat, protein, carbohydrate, minerals, and vitamins, and include a novel combination of lutein and docosahexaenoic acid. These and other essential elements or limitations of the infant formulas and corresponding methods of the present invention are described in detail hereinafter.

The term "infant" as used herein refers to individuals not more than about one year of age, and includes infants from 0 to about 4 months of age, infants from about 4 to about 8 months of age, infants from about 8 to about 12 months of age, low birth weight infants at less than 2,500 grams at birth, and preterm infants born at less than about 37 weeks gestational age, typically from about 26 weeks to about 34 weeks gestational age.

The term "infant formula" as used herein refers to a nutritional composition, free of egg phospholipids, which is designed for infants to contain sufficient protein, carbohydrate, fat, vitamins, and minerals to potentially serve as the sole source of nutrition when provided in sufficient quantity.

The term "ready-to-feed" as used herein, unless otherwise specified, refers to infant formulas in liquid form suitable for administration to an infant, including reconstituted powders, diluted concentrates, and manufactured liquids.

As used herein, all concentrations expressed as either "mcg/liter" or "mg/liter" refer to ingredient concentrations within the infant formulas of the present invention as calculated on a ready-to-feed or as fed basis, unless otherwise specified.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The infant formulas of the present invention may also be substantially free of any optional or selected essential ingredient or feature described herein, provided that the remaining formula still contains all of the required ingredients or features as described herein. In this context, the term "substantially free" means that the selected composition contains less than a functional amount of the optional ingredient, typically less than 0.1% by weight, and also including zero percent by weight of such optional or selected essential ingredient.

The infant formulas and corresponding methods of the present invention can comprise, consist of, or consist essentially of the essential elements and limitations of the invention described herein, as well as any additional or optional ingredients, components, or limitations described herein or otherwise useful in nutritional formula applications.

Lutein

The infant formulas of the present invention comprise lutein, concentrations of which must be at least about 50 mcg/liter of lutein. Any source of lutein is suitable for use herein provided that such a source is also known for or otherwise suitable for use in infant formulas and is compatible with the other selected ingredients in the formula, wherein the weight ratio of lutein (mcg/liter) to docosahexaenoic acid (mg/liter) in the formulas ranges from about 1:2 to about 10:1.

Lutein concentrations in the infant formulas of the present invention range from about 50 to about 1150 mcg/liter, including from about 75 to about 230 mcg/liter, and also including from about 100 to about 200 mcg/liter, as calculated on a ready-to-feed basis. All lutein concentrations and ratios referenced herein are calculated on a free lutein basis, unless otherwise specified.

The amount of lutein in the infant formulas must also be selected so that the weight ratio of lutein (mcg) to docosahexaenoic acid (mg) ranges from about 1:2 to about 10:1, including from about 1.5:1 to about 9:1, also including from about 1.7:1 to about 5:1.

The term "lutein" as used herein, unless otherwise specified, refers to one or more of free lutein, lutein esters, lutein salts, or other lutein derivatives or related structures as described or otherwise suggested herein. Lutein or lutein sources suitable for use in the infant formulas of the present invention include free lutein as well as esters, salts or other derivatives or related structures thereof, including those that conform to the formula:

The above formula includes the general structure of lutein and related derivatives or structures. Free lutein, for example, corresponds to the formula wherein $R_1$ and $R_2$ are both hydrogen, and includes cis and trans isomers thereof as well as salts thereof, e.g., sodium, potassium.

Lutein esters suitable for use in the infant formulas of the present invention include any lutein ester of the above formula wherein $R_1$ and $R_2$ are the same or different, and are nutritionally acceptable monovalent salts, hydrogen or an acyl residue of a carboxylic acid, provided that at least one of $R_1$ or $R_2$ is an acyl residue of a carboxylic acid. Suitable lutein esters include, as well, both cis and trans isomers. The $R_1$ and $R_2$ moieties are residues of a saturated or unsaturated $C_1$ to $C_{22}$ fatty carboxylic acids, non-limiting examples of which include formic, acetic, propionic, butyric, valeric, caproic, caprylic, capric, lauric, myristic, palmitic, stearic, and oleic acids.

Lutein for use herein includes any natural or synthetic source that is known for or is otherwise an acceptable source for use in oral nutritionals, including infant formulas. Lutein sources can be provided as individual ingredients or in any combination with other materials or sources, including sources such as multivitamin premixes, mixed carotenoid premixes, pure lutein sources, and inherent lutein from other fat or oil components in the infant formula. The lutein concentrations and ratios as described herein are calculated based upon added and inherent lutein sources. The infant formulas of the present invention preferably comprise at least about 25%, more preferably from about 50% to about 95%, by weight of total lutein as added lutein, the remainder being inherent lutein that accompanies added fats and oils.

Non-limiting examples of some suitable lutein sources for use herein include FloraGLO® Crystalline Lutein, available from Kemin Foods, Des Moines, Iowa, USA; and Xangold® Lutein Esters provided by Cognis, Cincinnati, Ohio, USA.

The infant formulas of the present invention include those preferred embodiments comprising a single source combination of free lutein and zeaxanthin, in a purified crystalline extract from the marigold flower (*Tagetes erecta*), wherein the free lutein represents from 85% to 95% by weight of the combination and the zeaxanthin represents from about 5% to about 15% by weight of the combination. The preferred lutein-zeaxanthin combination is available from Kemin Foods, Des Moines, Iowa, USA, under the FloraGLO® brand.

Docosahexaenoic Acid (DHA)

The infant formulas of the present invention comprise docosahexaenoic acid, an organic carboxylic acid having a chain length of 22 carbons with 6 double bonds beginning with the third carbon from the methyl end (22:6 n-3). Any source of docosahexaenoic acid is suitable for use herein provided that such a source is also known for or otherwise suitable for use in infant formulas and is compatible with the other selected ingredients in the formula.

Docosahexaenoic acid concentrations in the infant formulas of the present invention must be selected so that the resulting weight ratio of lutein to docosahexaenoic acid falls within the range as defined herein. Such concentrations most typically range from about 36 to 360 mg/liter, including from about 50 to about 144 mg/liter, and also including from about 72 to about 130 mg/liter, as calculated on a ready-to-feed basis.

The docosahexaenoic acid may be added to the infant formula as free fatty acids or as compounds or materials that can otherwise provide a source of such free fatty acids upon or following administration to the infant, including non-egg phospholipids and glyceride esters (mono-, di-, tri-) of docosahexaenoic acids. Polyunsaturated fatty acids and sources thereof are described in U.S. Pat. No. 6,080,787 (Carlson, et al.) and U.S. Pat. No. 6,495,599 (Auestad, et al.), which descriptions are incorporated by reference herein. Some non-limiting examples of suitable docosahexaenoic acid sources include fish oils, algal oils, other single cell oils, and combinations thereof.

The infant formulas of the present invention may further comprise, in addition to the docosahexaenoic acid as described herein, other long chain polyunsaturated fatty acids such as arachidonic acid (20:4 n-6), eicosapentaenoic acid or EPA (20:5 n-3), linoleic acid (18:2 n-6), γ-linolenic acid or GLA (18:3 n-6), α-linolenic acid (18:3 n-3), dihomo-γ-linolenic or DHGLA (20:3 n-6), α-linolenic (18:3 n-3), stearidonic acid (18:4 n-3), and combinations thereof. Such optional long chain polyunsaturated fatty acids may likewise be formulated into the infant formula as free fatty acids or as compounds or materials that can otherwise provide a source of such free fatty acids upon or following administration to the infant, including non-egg phospholipids and glyceride esters (mono-, di-, tri-) of docosahexaenoic acids.

Other Nutrients

The infant formulas of the present invention comprise fat, protein, carbohydrate, minerals, and vitamins, all of which are selected in kind and amount to meet the dietary needs of the intended infant population.

Many different sources and types of carbohydrates, fats, proteins, minerals and vitamins are known and can be used in the infant formulas of the present invention, provided that such nutrients are compatible with the added ingredients in the selected formulation and are otherwise suitable for use in an infant formula.

Carbohydrates suitable for use in the infant formulas of the present invention may be simple or complex, lactose-containing or lactose-free, or combinations thereof, non-limiting examples of which include hydrolyzed, intact, naturally and/or chemically modified cornstarch, maltodextrin, glucose polymers, sucrose, corn syrup, corn syrup solids, rice or potato derived carbohydrate, glucose, fructose, lactose, high fructose corn syrup and indigestible oligosaccharides such as fructooligosaccharides (FOS), galactooligosaccharides (GOS), and combinations thereof.

Proteins suitable for use in the infant formulas of the present invention include hydrolyzed, partially hydrolyzed, and non-hydrolyzed or intact proteins or protein sources, and can be derived from any known or otherwise suitable source such as milk (e.g., casein, whey), animal (e.g., meat, fish), cereal (e.g., rice, corn), vegetable (e.g., soy), or combinations thereof.

Proteins for use herein can also include, or be entirely or partially replaced by, free amino acids known for or otherwise suitable for use in infant formulas, non-limiting examples of which include alanine, arginine, asparagine, carnitine, aspartic acid, cystine, glutamic acid, glutamine, glycine, histidine, isoleucine, leucine, lysine, methionine, phenylalanine, proline, serine, taurine, threonine, tryptophan, taurine, tyrosine, valine, and combinations thereof. These amino acids are most typically used in their L-forms, although the corresponding D-isomers may also be used when nutritionally equivalent. Racemic or isomeric mixtures may also be used.

Fats suitable for use in the infant formulas of the present invention include coconut oil, soy oil, corn oil, olive oil, safflower oil, high oleic safflower oil, algal oil, MCT oil (medium chain triglycerides), sunflower oil, high oleic sunflower oil, palm and palm kernel oils, palm olein, canola oil, marine oils, cottonseed oils, and combinations thereof.

Vitamins and similar other ingredients suitable for use in the infant formulas of the present invention include vitamin A, vitamin D, vitamin E, vitamin K, thiamine, riboflavin, pyridoxine, vitamin B12, niacin, folic acid, pantothenic acid, biotin, vitamin C, choline, inositol, salts and derivatives thereof, and combinations thereof.

Minerals suitable for use in the infant formulas of the present invention include calcium, phosphorus, magnesium, iron, zinc, manganese, copper, chromium, iodine, sodium, potassium, chloride, and combinations thereof.

The infant formulas preferably comprise nutrients in accordance with the relevant infant formula guidelines for the targeted consumer or user population, an example of which would be the Infant Formula Act, 21 U.S.C. Section 350(a).

The infant formulas of the present invention also include those embodiments containing the carbohydrate, fat, and protein concentrations described in the following table.

TABLE 1

Infant Formula Nutrients[1]

| Nutrient | Range | gm/100 kcal | gm/liter[2] |
|---|---|---|---|
| Carbohydrate | 1$^{st}$ embodiment | 8-16 | 54-108 |
|  | 2$^{nd}$ embodiment | 9-13 | 61-88 |
| Fat | 1$^{st}$ embodiment | 3-8 | 20-54 |
|  | 2$^{nd}$ embodiment | 4-6.6 | 27-45 |
| Protein | 1$^{st}$ embodiment | 1-3.5 | 7-24 |
|  | 2$^{nd}$ embodiment | 1.5-3.4 | 10-23 |

[1]All numerical values may be modified by the term "about"
[2]From ready-to-feed liquid, reconstituted powder, or diluted concentrate The infant formulas of the present invention include those embodiments that comprise per 100 kcal of formula one or more of the following: vitamin A (from about 250 to about 750 IU), vitamin D (from about 40 to about 100 IU), vitamin K (greater than about 4 mcg), vitamin E (at least about 0.3 IU), vitamin C (at least about 8 mg), thiamine (at least about 8 g), vitamin B12 (at least about 0.15 g), niacin (at least about 250 g), folic acid (at least about 4 g), pantothenic acid (at least about 300 g), biotin (at least about 1.5 g), choline (at least about 7 mg), and inositol (at least about 4 mg).

The infant formulas of the present invention also include those embodiments that comprise per 100 kcal of formula one or more of the following: calcium (at least about 50 mg), phosphorus (at least about 25 mg), magnesium (at least about 6 mg), iron (at least about 0.15 mg), iodine (at least about 5 g), zinc (at least about 0.5 mg), copper (at least about 60 g), manganese (at least about 5 g), sodium (from about 20 to about 60 mg), potassium (from about 80 to about 200 mg), and chloride (from about 55 to about 150 mg).

Optional Ingredients

The infant formulas of the present invention may further comprise other optional ingredients that may modify the physical, chemical, aesthetic or processing characteristics of the compositions or serve as pharmaceutical or additional nutritional components when used in the targeted infant population. Many such optional ingredients are known or are otherwise suitable for use in nutritional products and may also be used in the infant formulas of the present invention, provided that such optional materials are compatible with the essential materials described herein and are otherwise suitable for use in an infant formula.

Non-limiting examples of such optional ingredients include preservatives, additional anti-oxidants, emulsifying agents, buffers, colorants, flavors, nucleotides and nucleosides, probiotics, prebiotics, lactoferrin and related derivatives, thickening agents and stabilizers, and so forth.

Product Form

The infant formulas of the present invention may be prepared as any product form suitable for use in infants, including reconstitutable powders, ready-to-feed liquids, and dilutable liquid concentrates, which product forms are all well known in the nutrition and infant formula arts.

The infant formulas of the present invention may have any caloric density suitable for the intended infant population, or provide such a density upon reconstitution of a powder embodiment or upon dilution of a liquid concentrate embodiment. Most common caloric densities for the infant formulas of the present invention are generally at least about 18 kcal/fl oz (609 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-30 kcal/fl oz, most typically from about 22-24 kcal/fl oz, formulas are more commonly used in pre-term of low birth weight infants, and the 20-21 kcal/fl oz (675-680 to 700 kcal/liter) formulas are more often used in term infants. Higher caloric feedings may be used with pre-term infants of low birth weight; such feedings are typically from about 27 kcal/fl oz (90-95 kcal/liter) to about 30 kcal/fl oz (1000-1015 kcal/liter).

For powder embodiments of the present invention, such powders are typically in the form of flowable or substantially flowable particulate compositions, or at least particulate compositions that can be easily scooped and measured with a spoon or similar other device, wherein the compositions can easily be reconstituted by the intended user with a suitable aqueous fluid, typically water, to form a liquid nutritional formula for immediate oral or enteral use. In this context, "immediate" use generally means within about 48 hours, most typically within about 24 hours, preferably right after reconstitution. These powder embodiments include spray dried, agglomerated, dry mixed or other known or otherwise effective particulate form. The quantity of a nutritional powder required to produce a volume suitable for one serving can vary.

The infant formulas of the present invention may be packaged and sealed in single or multi-use containers, and then stored under ambient conditions for up to about 36 months or longer, more typically from about 12 to about 24 months. For multi-use containers, these packages can be opened and then covered for repeated use by the ultimate user, provided that the covered package is then stored under ambient conditions (e.g., avoid extreme temperatures) and the contents used within about one month or so.

Retinal Health and Vision Development

The present invention is also directed to methods of administering the formulas to promote retinal health and vision development in infants. In this particular method, the infant formulas are administered to term or preterm infants as a sole source, primary source, or supplemental source of nutrition, wherein the formulas comprise fat, protein, carbohydrate, vitamins, and minerals, including docosahexaenoic acid and at least about 50 mcg/liter of lutein, wherein the weight ratio of lutein (mcg) to docosahexaenoic acid (mg) is from about 1:2 to about 10:1. Such a method may be applied to any formula embodiments described or otherwise suggested herein.

This particular method should therefore provide the infant with an effective amount of lutein to provide the stated benefits, including from about 7 to about 300 mcg/kg/day, including from about 14 to about 220 mcg/kg/day, and also including from about 22 to about 150 mcg/kg/day (of lutein per kg of body weight of the infant), wherein the weight ratio of lutein to docosahexaenoic acid is maintained within the ratios described herein.

Eye and vision development occurs at a rapid rate during the first year of life. At birth, infants can only see high-contrast objects at perhaps 25-30 cm away. During the next 6 months, the infant's retina develops enough to see and discern small details. And as an infant's vision develops, most of which will occur during the first year, the infant becomes better able to learn through visual stimulation now made possible with a newly developed sight. For infants, this visual learning then plays a key role in brain and cognitive development, especially during the first 2-3 years of life.

By promoting retinal health and vision development in infants, the infant formulas of the present invention may also help children develop their ability to visually learn as soon as possible, and to potentially accelerate brain and cognitive development associated with early visual stimulation through the developing retina of the eye. The infant formulas of the present invention are therefore useful in promoting vision development in infants, and consequently are useful in promoting secondary benefits such as associated cognitive and brain development through early visual stimulation.

This particular method of the present invention may be particularly useful in preterm infants to help accelerate the development of normal vision, to thus reduce the time needed to catch-up with development milestones set by their term infant counterparts.

Retinopathy of Prematurity

The infant formulas of the present invention are especially useful when administered to preterm infants to reduce the risk of retinopathy of prematurity. In accordance with such a method, the formulas are administered as a sole source, primary source, or supplemental source of nutrition, wherein the formulas comprise fat, protein, carbohydrate, vitamins, and minerals, including docosahexaenoic acid and at least about 50 mcg/liter of lutein, wherein the weight ratio of lutein (mcg) to docosahexaenoic acid (mg) is from about 1:2 to about 10:1. Such a method may be applied to any formula embodiments described or otherwise suggested herein.

Retinopathy of prematurity is a condition that often affects preterm infants and is most commonly characterized by abnormal development of retinal vessels in the eye possibly as a result of oxidative stress secondary to high oxygen tension. This affliction can occur to varying degrees, from slight vessel involvement with minimal or no impact on vision, to partial or complete retinal detachment leading to blindness. Historically, therapy for appropriate cases included laser treatment as well as cryotherapy.

This particular method should therefore provide the infant with an effective amount of lutein to provide the stated benefits, including from about 7 to about 300 mcg/kg/day, including from about 14 to about 220 mcg/kg/day, and also including from about 22 to about 150 mcg/kg/day (of lutein per kg of body weight of the infant), wherein the weight ratio of lutein to docosahexaenoic acid is maintained within the ratios described herein.

Method of Manufacture

The infant formulas of the present invention may be prepared by any known or otherwise effective technique suitable for making and formulating an infant formula or similar other formula, variations of which may depend upon variables such as the selected product form, ingredient combination, packaging and container selection, and so forth, for the desired infant formula. Such techniques and variations for any given formula are easily determined and applied by one of ordinary skill in the infant nutrition formulation or manufacturing arts.

The infant formulas of the present invention, including the exemplified formulas described hereinafter, can therefore be prepared by any of a variety of known or otherwise effective formulation or manufacturing methods. These methods most typically involve the initial formation of an aqueous slurry containing carbohydrates, proteins, lipids, stabilizers or other formulation aids, vitamins, minerals, or combinations thereof. The slurry is emulsified, pasteurized, homogenized, and cooled. Various other solutions, mixtures, or other materials may be added to the resulting emulsion before, during, or after further processing. This emulsion can then be further diluted, heat-treated, and packaged to form a ready-to-feed or concentrated liquid, or it can be heat-treated and subsequently processed and packaged as a reconstitutable powder, e.g., spray dried, dry mixed, agglomerated.

Other suitable methods for making nutritional formulas are described, for example, in U.S. Pat. No. 6,365,218 (Borschel, et al.), U.S. Pat. No. 6,589,576 (Borschel, et al.), U.S. Pat. No. 6,306,908 (Carlson, et al.), U.S. Patent Application 20030118703 A1 (Nguyen, et al.), which descriptions are incorporated herein by reference.

Experiment

The purpose of this experiment is to evaluate changes in visual acuity in animals fed infant formulas comprising either DHA or DHA with added lutein. Sixteen monkeys are fed one of two defined infant formulas during their first 12 weeks of life. One is a control formula—Similac® Advance® Infant formula, available from Abbott Laboratories, Columbus Ohio, and the other is an experimental formula including Similac® Advance® Infant Formula as a base, but with added carotenoids comprising lutein. The formulas include the following:

| Nutrient | Control formula | Experimental formula |
|---|---|---|
| DHA | 50 mg/L | 60 mg/L |
| Lutein | 0 mcg/L added (18 mcg/L inherent) | 117 mcg/L |
| Zeaxanthin | 0 mcg/L added (4 mcg/L inherent) | 36 mcg/L |
| Zeaxanthin/lutein | 22% | 31% |

The base formula (Similac® Advance® Infant formula) contains water, nonfat milk, lactose, high oleic safflower oil, soy oil, coconut oil, whey protein concentrate; *C. cohnii* oil, *M. alpina* oil, potassium citrate, calcium carbonate, ascorbic acid, mono- and diglycerides, soy lecithin, carrageenan, potassium chloride, magnesium chloride, sodium chloride, ferrous sulfate, choline chloride, choline bitartrate, taurine, m-inositol, d-alpha-tocopheryl acetate, L-carnitine, zinc sulfate, niacinamide, calcium pantothenate, riboflavin, vitamin A palmitate, cupric sulfate, thiamine chloride hydrochloride, pyridoxine hydrochloride, beta-carotene, folic acid, manganese sulfate, phylloquinone, biotin, sodium selenate, vitamin D3, cyanocobalamin and nucleotides (adenosine 5'-monophosphate, cytidine 5'-monophosphate, disodium guanosine 5'-monophosphate, disodium uridine 5'-monophosphate).

The monkeys are randomized to receive either the experimental (n=8) or control (n=8) formulas from birth to 12 weeks of life. The animals do not receive any milk from their mothers. Infants and mothers are separated at birth. During the study, the monkeys are exposed to light having the intensity and spectral characteristics of sunlight for 12 hours per day to simulate the light-induced oxidative stress potentially experienced by infants. During the study, the monkeys are evaluated for several parameters, including plasma lutein concentrations and sweep visual evoked potential (VEP).

Plasma Lutein

Plasma concentrations of lutein, lycopene, and beta-carotene are not significantly different between the monkeys fed the control and experimental formulas at birth (0 weeks of age). Plasma lutein concentrations are significantly higher in monkeys fed the experimental formula than monkeys fed the control formula at 4 ($p<0.001$), 8 ($p<0.001$), and 12 ($p<0.001$) weeks of age. Similarly, plasma lycopene concentrations are significantly higher in the experimental group compared to the control group at 4 ($p<0.001$), 8 ($p<0.001$), and 12 ($p<0.001$) weeks. Plasma beta-carotene concentrations are significantly greater in the experimental formula group than the control formula group at 4 ($p=0.005$) and 8 ($p=0.010$), but not 12 ($p=0.052$) weeks of age.

Visual Acuity

The monkeys are assessed for changes in visual acuity at 4, 8, and 12 weeks of life. Visual acuity is measured by sweep visual evoked potential (VEP), a method well known in the art for measuring visual evoked potential in infants. Visual acuity is measured by determining the smallest spatial frequency high contrast grating that evokes a measurable response from the visual cortex. The VEP from the primary cortical visual area is recorded using small silver disk EEG electrodes placed on the scalp with water-soluble electrode paste. The infant is held in an experimenter's lap while it gazes at a video monitor displaying phase-reversing black and white gratings. When necessary, the infant's attention will be drawn to the center of the screen with small dangling toys. During each "sweep", the spatial frequency of the grating will be decreased stepwise from above to below the subject's acuity threshold during a recording period of several seconds. The amplitude of the second harmonic of the VEP response, which reflects the response linked to the stimulus reversal rate, will be plotted as a function of spatial frequency to define the subject's acuity threshold (Neuringer M, Jeffrey B G: Visual development: neural basis and new assessment methods. *J Pediatr* 2003; 143:S87-S95).

Figure 1:
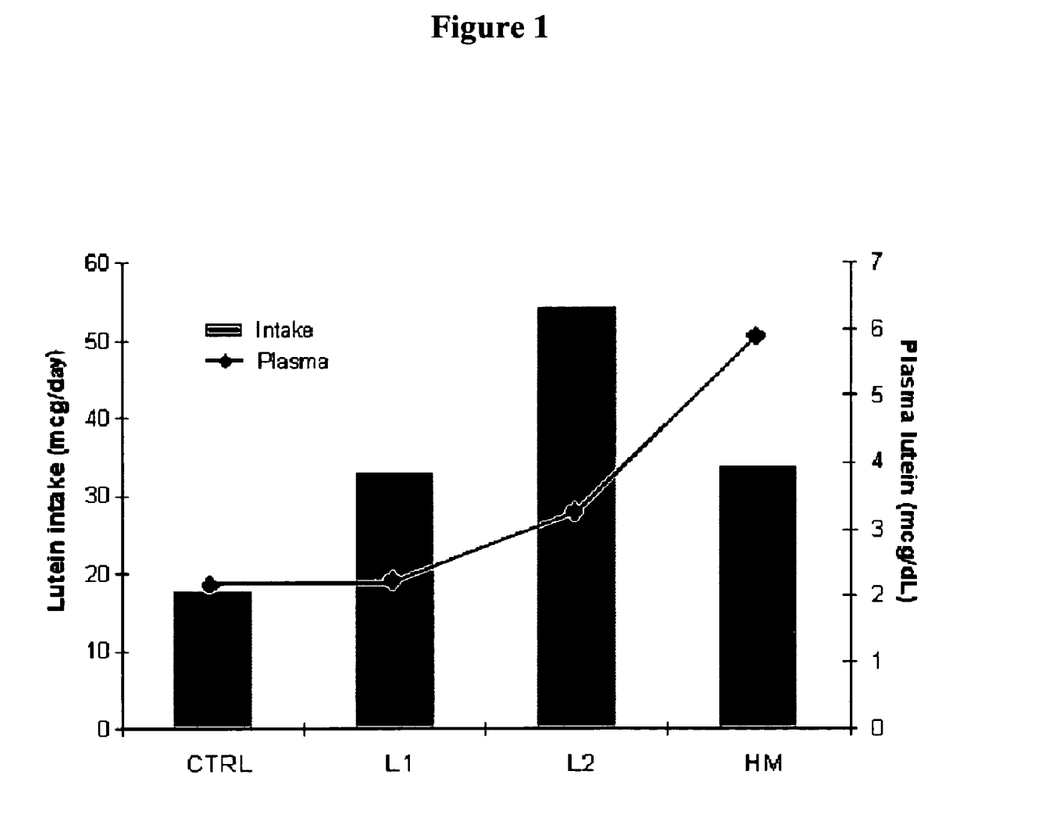
FIG. 1 is a graph of lutein intake (mcg/day) and corresponding plasma lutein concentrations (mcg/dl) in infant groups fed human milk (HM) or infant formulas containing varied concentrations of lutein [CTRL with 14.6 mcg lutein/liter (no added lutein, all lutein inherent in ingredients); L1 with 32.6 mcg lutein/liter (approximately 18 mcg/liter added lutein, remainder inherent), L2 with 52.6 mcg lutein/liter (approximately 38 mcg/liter added lutein, remainder inherent).
Figure 2:
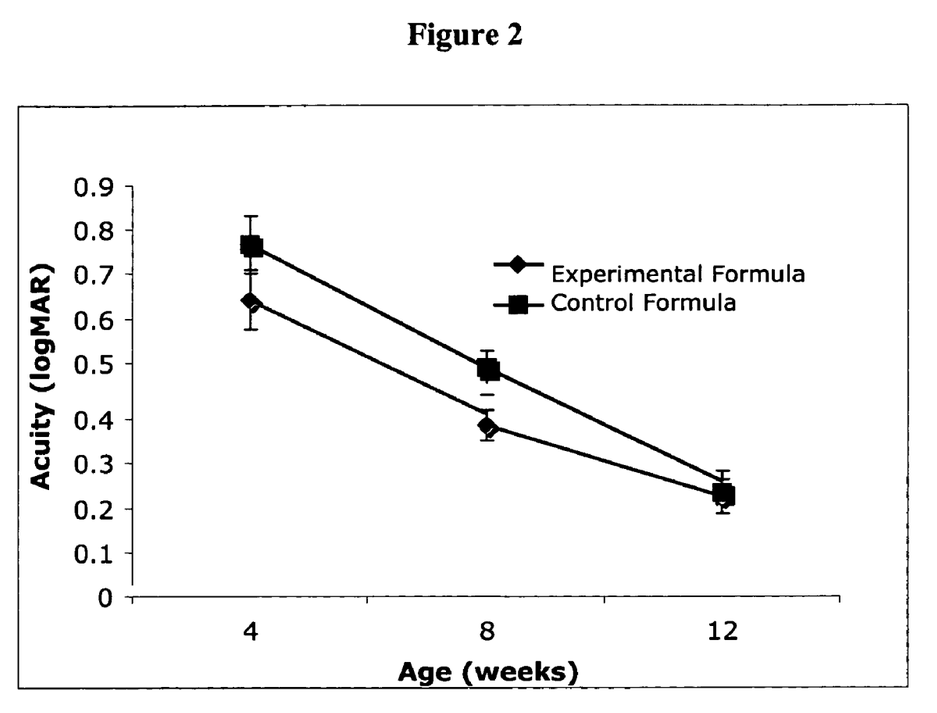
FIG. 2 is a graph showing visual acuity as measured by sweep visual evoked potential (logMAR) in monkeys at 4, 8, and 12 weeks of age. The monkeys are fed infant formula with either DHA and added lutein (n=8) or DHA without added lutein (n=8) during a 12 week feeding period.

VEP scores from the study are summarized in the FIG. 1 graph. Lower VEP (logMAR) scores are indicative of better visual acuity. Although VEP scores decreased (i.e., visual acuity improved) for all monkeys during the 12 week testing period, as expected, the VEP scores at 8 weeks were surprisingly lower in the experimental group (added lutein+DHA formula) than in the control group (DHA without added lutein formula) (4 weeks, p=0.412, etc.)

The data suggest accelerated development in infant monkeys fed the experimental formula at 8 weeks of life—specifically in visual acuity as measured by VEP values. To extrapolate the data to human infants, the eye development in monkeys at ages of 4, 8, and 12 weeks corresponds to the eye development in human infants at 4, 8, and 12 months, respectively. The data therefore suggests that even in a human infant, the experimental formula would improve visual acuity at between about 4 and about 12 months of life.

EXAMPLES

The following examples represent specific embodiments within the scope of the present invention, each of which is given solely for the purpose of illustration and is not to be construed as limitations of the present invention, as many variations thereof are possible without departing from the spirit and scope of the invention. All exemplified amounts are weight percentages based upon the total weight of the composition, unless otherwise specified.

Examples 1.1-1.3

The following are examples of milk-based, ready-to-feed, infant formulas of the present invention, including a method of using and making the formulas. The formula ingredients for each batch are listed in the table below.

| Ingredient | Example 1.1 Amount per 454 kg | Example 1.2 Quantity per 454 kg | Example 1.3 Quantity per 454 kg |
| --- | --- | --- | --- |
| Water | QS | QS | QS |
| Lactose | 27 kg | 27 kg | 27 kg |
| ARA-containing oil (40% ARA) | 0.167 kg | 0.167 kg | 0.167 kg |
| DHA-containing oil (40% DHA) | 0.063 kg | 0.095 kg | 0.145 kg |
| Non-fat dry milk | 11.33 kg | 11.33 kg | 11.33 kg |
| High oleic safflower oil | 6.5 kg | 6.5 kg | 6.5 kg |
| Mono- and di-glycerides | 0.162 kg | 0.162 kg | 0.162 kg |
| Soybean oil | 5 kg | 5 kg | 5 kg |
| Whey protein | 2.8 kg | 2.8 kg | 2.8 kg |
| Calcium carbonate | 0.211 kg | 0.211 kg | 0.211 kg |
| Coconut oil | 4.6 kg | 4.6 kg | 4.6 kg |
| Citric acid | 0.014 kg | 0.014 kg | 0.014 kg |
| Potassium citrate | 0.245 kg | 0.245 kg | 0.245 kg |

-continued

| Ingredient | Example 1.1 Amount per 454 kg | Example 1.2 Quantity per 454 kg | Example 1.3 Quantity per 454 kg |
| --- | --- | --- | --- |
| Ascorbic acid | 178 g | 178 g | 178 g |
| Lecithin | 162 g | 162 g | 162 g |
| Magnesium chloride | 25 g | 25 g | 25 g |
| Potassium chloride | 88 g | 88 g | 88 g |
| Ferrous sulfate | 26 g | 26 g | 26 g |
| Carrageenan | 136 g | 136 g | 136 g |
| Choline chloride | 25 g | 25 g | 25 g |
| Nucleotide and choline premix [3] | 133 g | 133 g | 133 g |
| Riboflavin | 1 g | 1 g | 1 g |
| L-Carnitine | 1.5 g | 1.5 g | 1.5 g |
| Potassium hydroxide | 998 g | 998 g | 998 g |
| Lutein solution (5% active) [4] | 0.882 g | 1.323 g | 1.764 g |
| Water soluble vitamin premix [1] | 65 g | 65 g | 65 g |
| Vitamin ADEK premix [2] | 21 g | 21 g | 21 g |
| Vitamin A | 0.4 g | 0.4 g | 0.4 g |
| Beta-carotene soln (30% active) | 0.0485 g | 0.0485 g | 0.0485 g |
| Total Lutein (mcg/liter) | 100 | 150 | 200 |
| Total DHA (mg/liter) | 50 | 75 | 115 |
| Ratio - Lutein (mcg):DHA (mg) | 2 | 2 | 1.74 |

[1] premix contains (per 65 g) 19.8 g taurine, 14.4 g inositol, 6.7 g zinc sulfate, 4.2 g niacinamide, 2.6 g calcium pantothenate, 2.3 g ferrous sulfate, 0.8 g cupric sulfate, 0.6 g thiamine, 0.3 g riboflavin, 0.26 g pyridoxine, 0.1 g folic acid, 0.07 g manganese sulfate, 0.03 g biotin, 0.025 g sodium selenate, 0.002 g cyanocobalamin
[2] premix contains (per 21 g) 4.0 g alpha-tocopherol acetate, 0.8 g vitamin A palmitate, 0.05 g phylloquinone, 0.006 g vitamin D3
[3] premix contains (per 133 g): 23 g choline bitartrate, 15 g 5'-CMP, 11 g 5'-GMP, 10 g 5'-UMP, 6 g 5'-AMP
[4] FloraGLO ® Crystalline Lutein, Kemin Foods, Des Moines, Iowa, USA The exemplified formulas may be prepared by making at least three separate slurries that are later blended together, heat treated, standardized, packaged and sterilized. Initially, a carbohydrate-mineral slurry is prepared by dissolving lactose in water at 65-71° C., followed by the addition of magnesium chloride, potassium citrate, potassium chloride, choline chloride, and citric acid. The resulting slurry is held with agitation at 55-65° C. for not longer than eight hours until it is later blended with the other prepared slurries.

A protein-fat slurry is prepared by combining high oleic safflower oil, soybean oil, and coconut oil at 55-60° C., followed by the addition of vitamin ADEK premix, mono- and diglycerides, lecithin, carrageenan, vitamin A, ARA oil, and DHA oil. Whey protein and calcium carbonate are then added. The resulting protein-oil slurry is held under moderate agitation at 40-43° C. for no longer than two hours until it is later blended with the other formed slurries.

The carbohydrate-mineral slurry is then combined with water and non-fat dry milk and agitated for 10 minutes. The protein-oil slurry is then added and the resulting mixture agitated for at least 10 minutes. Lutein and beta-carotene are then added to the blend and agitated for at least 15 minutes. The pH of the resulting blend is adjusted to 6.68-6.75 with 1N potassium hydroxide.

After waiting for a period of not less than one minute nor greater than two hours, the resulting blend is heated to 71-82° C. and dearated under vacuum, emulsified through a single stage homogenizer at 900-1100 psig, and then heated to 99-110° C., and then heated again to 146° C. for about 5 seconds. The heated blend is passed through a flash cooler to reduce the temperature to 99-110° C. and then through a plate cooler to further reduce the temperature to 71-76° C. The cooled blend is then homogenized at 3900-4100/400-600 psig, and then held at 74-80° C. for 16 seconds, and then cooled to 1-7° C. Samples are taken for microbiological and analytical testing. The mixture is held under agitation.

A water-soluble vitamin (WSV) solution and an ascorbic acid solution are prepared separately and added to the processed blended slurry. The vitamin solution is prepared by adding the following ingredients to 9.4 kg of water with agitation: potassium citrate, ferrous sulfate, WSV premix, L-carnitine, riboflavin, and the nucleotide-choline premix. The ascorbic acid solution is prepared by adding potassium citrate and ascorbic acid to a sufficient amount of water to dissolve the ingredients. The vitamin and ascorbic acid solutions are then added to the blend, and the pH of the blend adjusted to 7-10 with 45% potassium hydroxide solution.

Based on the analytical results of the quality control tests, an appropriate amount of water is added to the batch with agitation to achieve the desired total solids. The product pH may be adjusted to achieve optimal product stability. The completed product is then placed in suitable containers and subjected to terminal sterilization.

The resulting formulas are fed to infants as a sole source of nutrition during the first 6 to 12 months of life to provide each infant with 7-300 µg/kg/day of lutein. The formulas provide improved retinal health and vision development as described herein.

Examples 2.1-2.3

The following are examples of soy-based, powder, infant formulas of the present invention, including a method of using and making the formulas. The formula ingredients for each batch are listed in the table below.

soluble vitamin premix, all with agitation. Beta-carotene (BASF, Mount Olive, N.J.), and lutein (Kemin, Des Moines, Iowa) are added to the oil blend and agitated until well dispersed. Soy protein isolate and methionine are then added to the oil blend, and the resulting mixture agitated and held at 54.0-60° C. until used later during the manufacturing process.

The carbohydrate-mineral slurry is then prepared. Potassium chloride, sodium chloride, magnesium chloride, and potassium iodide are added to water 60-65° C., followed by di- and tri-calcium phosphates, all with agitation. Corn syrup is then added with agitation, and the slurry held at 54-60° C. until used later during the manufacturing process.

The carbohydrate-mineral slurry is added to the oil blend. Additional water is added as necessary. The ARA and DHA oils are added to the blend. The pH of the resulting mixture is adjusted to 6.75-6.85 using KOH solution. The adjusted mixture is then held at 54-60C under agitation for at least 15 minutes.

The resulting mixture is then heated to 74-79C and dearated under vacuum, emulsified through a single stage homogenizer at 0-2.76 Mpa, passed through a two-stage homogenizer at 6.2-7.6 MPa and 2.1-3.4 MPa. The homogenized mixture is held at 73-79C for 16 seconds and then cooled to 1-7C. Samples are taken for microbiological and analytical testing. The mixture is held under agitation.

A calcium carbonate solution may be prepared for use in adjusting the calcium level of the mixture if outside of specification.

A vitamin stock solution containing a water soluble vitamin premix with trace minerals and taurine is prepared.

| INGREDIENT | Example 2.1 Amount per 454 kg | Example 2.2 Amount per 454 kg | Example 2.3 Amount per 454 kg |
|---|---|---|---|
| High oleic safflower oil | 52.1 kg | 52.1 kg | 52.1 kg |
| Coconut oil | 35.2 kg | 35.2 kg | 35.2 kg |
| Soy oil | 38.1 kg | 38.1 kg | 38.1 kg |
| ARA-containing oil (40% ARA) | 1.3 kg | 1.3 kg | 1.3 kg |
| DHA-containing oil (40% DHA) | 0.381 kg | 0.762 kg | 0.876 kg |
| Oil soluble vitamin premix | 0.173 kg | 0.173 kg | 0.173 kg |
| β-carotene solution (30% active) | 0.0004 kg | 0.0004 kg | 0.0004 kg |
| Ascorbyl palmitate | 0.162 kg | 0.162 kg | 0.162 kg |
| Soy protein isolate | 66.1 kg | 66.1 kg | 66.1 kg |
| Corn syrup | 236.0 kg | 236.0 kg | 236.0 kg |
| Calcium phosphate (di and tribasic) | 8.0 kg | 8.0 kg | 8.0 kg |
| Ferrous sulfate | 0.138 kg | 0.138 kg | 0.138 kg |
| Lutein solution (5.0% active) [1] | 7.06 g | 10.5903 g | 14.200 g |
| Water soluble vitamin premix trace minerals/taurine | 0.65 kg | 0.65 kg | 0.65 kg |
| Choline chloride | 0.23 kg | 0.23 kg | 0.23 kg |
| Potassium iodide | 0.0005 kg | 0.0005 kg | 0.0005 kg |
| Methionine | 0.722 kg | 0.722 kg | 0.722 kg |
| Ascorbic acid | 0.72 kg | 0.72 kg | 0.72 kg |
| Potassium hydroxide (45% solution) | 1.2 kg | 1.2 kg | 1.2 kg |
| Potassium chloride | 0.87 kg | 0.87 kg | 0.87 kg |
| Magnesium Chloride | 0.4 kg | 0.4 kg | 0.4 kg |
| Carnitine | 0.05 kg | 0.05 kg | 0.05 kg |
| Total Lutein (mcg/liter as fed) | 100 | 150 | 200 |
| Total DHA (mg/liter as fed) | 50 | 100 | 115 |
| Ratio - Lutein (mcg):DHA (mg) as fed | 2 | 2 | 1.74 |

[1] FloraGLO ® Crystalline Lutein, Kemin Foods, Des Moines, Iowa, USA

The first step in the preparation of the exemplified powder is the preparation of the oil blend. Soy oil, coconut oil and high oleic safflower oil are combined in a suitable container or tank at 60-65° C. with agitation. Ascorbyl palmitate and mixed tocopherols are added to the tank, followed by the oil Potassium citrate and ferrous sulfate are added to water at 37-66° C. The vitamin premix is then added and the mixture agitated. The choline chloride and carnitine are added and then the required amount of this vitamin mixture is added to the batch.

An ascorbic acid solution is prepared and added slowly to the batch with agitation for at least 10 minutes. The batch is then preheated to 74-79° C. The batch is then held for 5 seconds at 107-111° C. using direct steam injection. The batch is then cooled to 71-82° C. before being pumped to a spray dryer and dried to a flowable powder. The batch is then packaged in suitable containers and sealed under a headspace of less than 2.0% oxygen.

The exemplified powders are reconstituted with water to a caloric density of 676 kcal/liter. The resulting liquid formulas are fed to infants as a sole source of nutrition during the first 6 to 12 months of life to provide 7-300 μg/kg/day of lutein. The formula provides improved retinal health and vision development as described herein.

Examples 3.1-3.3

The following are examples of milk-based, powder, infant formulas of the present invention, including a method of using and making the formula. The formula ingredients for each batch are listed in the table below.

chloride, and sodium citrate, all with agitation. The resulting carbohydrate-mineral slurry is held at 54-60° C. under agitation until used later during the manufacturing process.

A protein-fat slurry is prepared by combining high oleic safflower oil, coconut oil, soy oil, and MCT oil at 40.5-49° C., followed by ascorbyl palmitate, mixed tocopherols, vitamin A palmitate, and the vitamin ADEK premix, all with agitation. Lutein (Kemin, Des Moines, Iowa), is then added with agitation. Whey protein concentrate is then added to the slurry, followed by calcium carbonate and calcium phosphate tribasic, all with agitation. The completed protein-fat slurry is held under moderate agitation at 54-60° C. for no longer than twelve hours until it is blended with the other prepared slurries.

The carbohydrate-mineral slurry is transferred to a tank in which a sufficient amount of water is added to create a final blend slurry of approximately 50% solids. Non-fat dry milk is then added to the blend and allowed to solubilize. The protein-fat slurry is then added and the entire blend slurry is

| Ingredient Name | Example 3.1 Amount per 454 kg | Example 3.2 Amount per 454 kg | Example 3.3 Amount per 454 kg |
|---|---|---|---|
| Soy oil | 35.8 kg | 35.8 kg | 35.8 kg |
| Coconut oil | 23.8 kg | 23.8 kg | 23.8 kg |
| MCT oil (medium chain triglyceride) | 32.1 kg | 32.1 kg | 32.1 kg |
| High Oleic Safflower oil | 34.6 kg | 34.6 kg | 34.6 kg |
| Ascorbyl palmitate | 0.157 kg | 0.157 kg | 0.157 kg |
| Vitamin A palmitate | 0.002 kg | 0.002 kg | 0.002 kg |
| Vitamin ADEK premix [1] | 0.192 kg | 0.192 kg | 0.192 kg |
| Mixed tocopherols | 0.075 kg | 0.075 kg | 0.075 kg |
| Lutein solution (20% active) [4] | 7.060 g | 10.590 g | 13.714.200 g |
| Whey protein concentrate | 32.7 kg | 32.7 kg | 32.7 kg |
| Calcium carbonate | 1.2 kg | 1.2 kg | 1.2 kg |
| Lactose | 54.5 kg | 54.5 kg | 54.5 kg |
| Corn syrup solids | 117.1 kg | 117.1 kg | 117.1 kg |
| Magnesium chloride | 0.724 kg | 0.724 kg | 0.724 kg |
| Potassium citrate | 2.8 kg | 2.8 kg | 2.8 kg |
| Sodium chloride | 0.39 kg | 0.39 kg | 0.39 kg |
| Sodium citrate | 0.001 kg | 0.001 kg | 0.001 kg |
| Non-fat dried milk | 116.9 kg | 116.9 kg | 16.9 kg |
| Calcium phosphate tribasic | 1.8 kg | 1.8 kg | 1.8 kg |
| ARA-containing oil (40% ARA) | 1.3 kg | 1.3 kg | 1.3 kg |
| DHA-containing oil (40% DHA) | 0.43 kg | 0.65 kg | 1.00 kg |
| Ascorbic acid | 1.29 kg | 1.29 kg | 1.29 kg |
| Potassium hydroxide 1N solution | 9.8 kg | 9.8 kg | 9.8 kg |
| Ferrous sulfate | 0.168 kg | 0.168 kg | 0.168 kg |
| Carnitine | 0.136 kg | 0.136 kg | 0.136 kg |
| Choline chloride | 0.182 kg | 0.182 kg | 0.182 kg |
| Vit. and trace mineral premix [2] | 0.825 kg | 0.825 kg | 0.825 kg |
| Inositol | 0.734 kg | 0.734 kg | 0.734 kg |
| Nucleotide, choline bitartrate premix [3] | 1.1 kg | 1.1 kg | 1.1 kg |
| Total Lutein (mcg/liter as fed) | 100 | 150 | 200 |
| Total DHA (mg/liter as fed) | 50 | 75 | 115 |
| Ratio - Lutein (mcg):DHA (mg) as fed | 2 | 2 | 1.74 |

[1] premix provides 71 gm d-alpha-tocopheryl acetate, 7.29 gm Vitamin A palmitate, 0.422 gm phylloquinone, and 0.051 gm Vitamin D3 to the product.
[2] premix provides 252 gm taurine, 183 gm inositol, 84.5 gm zinc sulfate, 53.8 gm niacinamide, 32.6 gm calcium pantothenate, 29 gm ferrous sulfate, 10.1 gm cupric sulfate, 8.4 gm thiamine, 3.7 gm riboflavin, 3.4 gm pyridoxine (HCl), 1.1 gm folic acid, 1.0 gm manganese sulfate, 0.3 gm biotin, 0.2 gm sodium selenate, and 0.03 gm cyanocobalamin to the product.
[3] premix provides 188 gm choline bitartrate, 118 gm cytidine 5'-monophosphate, 92 gm disodium guanosine 5'-monophosphate, 80 gm disodium undine 5'-monophosphate, and 51 gm adenosine 5'-monophosphate to the product.
[4] FloraGLO ® Crystalline Lutein, Kemin Foods, Des Moines, Iowa, USA This powder formula is manufactured by preparing at least two slurries that are later blended together, heat treated, standardized, spray dried and packaged. Initially, a carbohydrate-mineral slurry is prepared (45-50% solids) by dissolving lactose in water at 66-76° C. Corn syrup solids are then added and allowed to dissolve, followed by the addition of magnesium chloride, potassium citrate, sodium chloride, choline allowed to agitate for at least 15 minutes. The resulting blend is maintained at 60-65° C. The blend pH is adjusted to 6.7-6.9 with 1N KOH.

After waiting for a period of not less than one minute nor greater than two hours, the resulting blend is heated to 71-79° C., emulsified at 2.75-4.1 Mpa, and then heated to 115-127° C. for about 5 seconds using direct steam injection. The heated emulsion is then flash cooled to 87-99° C., and homogenized at 9.7-11.0/2.75-4.1 MPa. The homogenized slurry is then cooled to 1.6-7.2° C. Samples are taken for microbiological and analytical testing. The mixture is held under agitation.

A vitamin-trace mineral solution is prepared by adding the following ingredients to the required amount of water, under agitation: potassium citrate, ferrous sulfate, carnitine, vitamin and the trace mineral premix, inositol, and nucleotide and choline bitartrate premix. The vitamin-trace mineral solution is then added to the homogenized slurry under agitation.

An ascorbic acid solution is prepared by adding potassium citrate and ascorbic acid to water with agitation, and then adding the aqueous mixture to the homogenized slurry under agitation.

The product is preheated to 65.5-77° C. The product is then held at 82-90.5° C. for 5 seconds before being flash cooled to 71-82° C. and pumped to the spray dryer. The product is spray dried to produce a desired free-flowing powder. The resulting powder is packaged under nitrogen to maximize product stability and flavor.

The exemplified powders are reconstituted with water to a caloric density of 676 kcal/liter. The resulting liquid formulas are fed to infants as a sole source of nutrition during the first 6 to 12 months of life to provide 7-300 µg/kg/day of lutein. The formula provides improved retinal health and vision development as described herein.

Examples 4.1-4.3

The following are examples of concentrated human milk fortifier liquids of the present invention, including a method of using and making the formula. The formula ingredients for each batch are listed in the following table.

| Ingredient Name | Example 4.1 Gm per kg | Example 4.2 Gm per kg | Example 4.3 Gm per kg |
| --- | --- | --- | --- |
| Sucrose | 125.5 | 125.5 | 125.5 |
| Milk protein isolate | 64.6 | 64.6 | 64.6 |
| Coconut oil | 30.2 | 30.2 | 30.2 |
| Whey protein concentrate | 24.4 | 24.4 | 24.4 |
| MCT Oil | 21.9 | 21.9 | 21.9 |
| Soy Oil | 21.9 | 21.9 | 21.9 |
| Tricalcium phosphate | 14.4 | 14.4 | 14.4 |
| Potassium chloride | 5.18 | 5.18 | 5.18 |
| Calcium carbonate | 3.44 | 3.44 | 3.44 |
| Magnesium phosphate | 3.05 | 3.05 | 3.05 |
| Potassium citrate | 1.32 | 1.32 | 1.32 |
| DHA (docosahexaenoic acid) oil | 0.2 | 0.2 | 0.2 |
| Soy lecithin | 0.756 | 0.756 | 0.756 |
| ARA (arachidonic acid) oil | 0.729 | 0.729 | 0.729 |
| Dipotassium phosphate | 0.596 | 0.596 | 0.596 |
| Monopotassium phosphate | 0.466 | 0.466 | 0.466 |
| Vitamin E | 0.357 | 0.357 | 0.357 |
| Sodium chloride | 0.170 | 0.170 | 0.170 |
| KOH 5% solution | Q.S. | Q.S. | Q.S. |
| Lutein (from 20% solution) [1] | 0.00018 | 0.00064 | 0.00091 |
| m-Inositol | 0.0698 | 0.0698 | 0.0698 |
| Ascorbic acid | 0.913 | 0.913 | 0.913 |
| Taurine | 0.0663 | 0.0663 | 0.0663 |
| Niacinamide | 0.0582 | 0.0582 | 0.0582 |
| Vitamin A | 0.0494 | 0.0494 | 0.0494 |
| Zinc sulfate | 0.0461 | 0.0461 | 0.0461 |
| Calcium pantothenate | 0.0286 | 0.0286 | 0.0286 |
| Ferrous sulfate | 0.0136 | 0.0136 | 0.0136 |
| Cupric sulfate | 0.00836 | 0.00836 | 0.00836 |
| Riboflavin | 0.00763 | 0.00763 | 0.00763 |
| Thiamine chloride HCL | 0.00507 | 0.00507 | 0.00507 |
| Pyridoxine HCL | 0.00459 | 0.00459 | 0.00459 |
| Folk acid | 0.000778 | 0.000778 | 0.000778 |
| Manganese Sulfate | 0.000573 | 0.000573 | 0.000573 |
| Biotin | 0.000507 | 0.000507 | 0.000507 |
| Vitamin K | 0.000835 | 0.000835 | 0.000835 |
| Vitamin D3 | 0.000235 | 0.000235 | 0.000235 |
| Sodium selenate | 0.0000491 | 0.0000491 | 0.0000491 |
| Potassium iodide | 0.0000105 | 0.0000105 | 0.0000105 |
| Cyanocobalamin | 0.0000103 | 0.0000103 | 0.0000103 |
| Total Lutein (mcg/liter as fed) | 200 | 700 | 1000 |
| Total DHA (mg/liter as fed) | 200 | 200 | 200 |
| Ratio - Lutein (mcg):DHA (mg) as fed | 1.5 | 3.2 | 4.5 |

[1] FloraGLO ® Crystalline Lutein, Kemin Foods, Des Moines, Iowa, USA

The ingredients listed in the preceeding table are combined and processed to form a concentrated human milk fortifier embodiment of the present invention. One method of preparing such an embodiment is described below.

An initial intermediate blend is prepared by heating to 32-37° C. the specified amounts of coconut oil, MCT oil, soy oil, DHA oil and AA oil, all with agitation. A soy lecithin emulsifier is added with agitation to the heated blend and allowed to dissolve. Vitamins A, D, and K, Natural Vitamin E, and lutein are then added with agitation to the developing blend. Milk protein isolate (25.8 kg) and the specified amounts of ultra micronized tricalcium phosphate and calcium carbonate are added to the blend. The resulting intermediate blend is maintained at 26-48° C. under moderate agitation for a period of time not to exceed six hours before being added to the aqueous protein blend described below.

An aqueous protein blend is then prepared by heating 573 kg of ingredient water at 48-60° C., and then adding to it with agitation milk protein isolate (38.8 kg) and the specified amount of whey protein concentrate. Thereafter, and with agitation, the entire intermediate blend described above is added to the aqueous protein blend. The following ingredients are then added to the resulting blend in the following order: potassium citrate, dipotassium phosphate, monopotassium phosphate, magnesium phosphate, sodium chloride, potassium chloride, potassium iodide and sucrose. After no less than five minutes, the blend pH is adjusted to 6.60-6.80 using a 1N KOH solution, and thereafter maintained at 51-60° C., for a period of time not to exceed two hours before further processing.

The pH adjusted blend is then homogenized using one or more in-line homogenizers at pressures from 1000-4000 psig with or without a second stage homogenization from 100-500 psig followed by heat treatment using a HTST (high temperature short time, 74° C. for 16 seconds) or UHTST (ultra-high temperature short time, 132-154° C. for 5-15 seconds) process. The choice of UHTST or HTST is normally made based upon a review of the bioburden of each of the ingredients in the formulation. After the appropriate heat treatment, the batch is cooled in a plate cooler to 1.0-5.0° C. and then transferred to a refrigerated holding tank, where it is subjected to analytical testing and then standardized to finished product specifications, which includes the addition of an ascorbic acid solution and a water-soluble vitamin and trace mineral solution, all of which is prepared separately before adding to the previously described refrigerated batch.

The ascorbic acid solution is prepared by adding the specified amount of ascorbic acid to 11.1 kg of 1N KOH solution with agitation. The water-soluble vitamin and trace mineral solution is prepared by heating 25.2 kg of ingredient water to 37° C. to 48° C. The water soluble vitamins and trace minerals are added to the water as a premix which contains m-inositol, taurine, niacinamide, zinc sulfate, calcium pantothenate, ferrous sulfate, cupric sulfate, riboflavin, thiamine hydrochloride, pyridoxine hydrochloride, folic acid, manganese sulfate, biotin, sodium selenate, and cyanocobalamin. As noted above, both solutions are then added to the refrigerated batch, all with agitation. As part of batch standardization, the appropriate amount of ingredient dilution water is then added to the batch for a target total solids level of 31%, and the pH adjusted to 7.1 with a 1N KOH solution. The batch is filled into suitably sized containers containing 5 ml of product.

The exemplified human milk fortifier concentrates are combined with human milk (5 ml concentrate with 20-25 ml human milk). The fortified human milk is then fed to pre-term infants to provide 7-300 μg/kg/day of lutein. The formula provides improved retinal health and vision development as described herein, including reduced risk of retinopathy of prematurity.

Examples 5.1-5.3

This example illustrates a ready-to-feed, preterm infant formula embodiment of the present invention. This formula is similar to Similac® Special Care® Advance® with Iron Premature Infant formula, a preterm infant formula available from Abbott Laboratories, Columbus, Ohio, except for the increased lutein concentrations and subsequent lutein to docosahexaenoic acid ratios.

The preterm infant formula includes nonfat milk, corn syrup solids, lactose, medium chain triglycerides, whey protein concentrate, soy oil, coconut oil, *C. cohnii* oil (source of docosahexaenoic acid), *M. alpina* oil (source of arachidonic acid), calcium phosphate, calcium carbonate, potassium citrate, ascorbic acid, magnesium chloride, soy lecithin, mono- and diglycerides, m-inositol, sodium citrate, carrageenan, ferrous sulfate, choline bitartrate, taurine, choline chloride, niacinamide, d-alpha-tocopheryl acetate, L-carnitine, zinc sulfate, potassium chloride, potassium phosphate dibasic, calcium pantothenate, cupric sulfate, vitamin A palmitate, riboflavin, thiamine chloride hydrochloride, pyridoxine hydrochloride, folic acid, beta-carotene, manganese sulfate, biotin, phylloquinone, sodium selenate, vitamin D3, cyanocobalamin and nucleotides (cytidine 5'-monophosphate, disodium guanosine 5'-monophosphate, disodium uridine 5'-monophosphate, adenosine 5'-monophosphate).

The above-referenced ingredients are formulated together by conventional methods to provide the following nutrition profile:

| Nutrients | Example 5.1<br>Amount per 100 kcal<br>(or 123 ml) | Example 5.2<br>Amount per 100 kcal<br>(or 123 ml) | Example 5.3<br>Amount per 100 kcal<br>(or 123 ml) |
| --- | --- | --- | --- |
| Protein (from nonfat milk, whey protein concentrate) | 3.00 g | 3.00 g | 3.00 g |
| Fat (form 50:30:18.3 mix of MCT oil, soy oil, and coconut oils; ----- mg DHA, ----- mg ARA; 700 mg linoleic acid) | 5.43 g | 5.43 g | 5.43 g |
| Carbohydrate (source - 50:50 mix of corn syrup solids, lactose) | 10.3 g | 10.3 g | 10.3 g |
| Lutein | 18.4 mcg | 37 mcg | 9141 mcg |
| Vitamin A | 1250 IU | 1250 IU | 1250 IU |
| Vitamin D | 150 IU | 150 IU | 150 IU |
| Vitamin E | 4.0 IU | 4.0 IU | 4.0 IU |
| Vitamin K | 12 mcg | 12 mcg | 12 mcg |
| Thiamine | 250 mcg | 250 mcg | 250 mcg |
| Riboflavin | 620 mcg | 620 mcg | 620 mcg |
| Vitamin B6 | 250 mcg | 250 mcg | 250 mcg |
| Vitamin B12 | 0.55 mcg | 0.55 mcg | 0.55 mcg |
| Niacin | 5000 mcg | 5000 mcg | 5000 mcg |
| Folic acid | 37 mcg | 37 mcg | 37 mcg |
| Pantothenic acid | 1900 mcg | 1900 mcg | 1900 mcg |
| Biotin | 37.0 mcg | 37.0 mcg | 37.0 mcg |
| Ascorbic acid | 37 mg | 37 mg | 37 mg |
| Choline | 10 mg | 10 mg | 10 mg |
| Inositol | 40.0 mg | 40.0 mg | 40.0 mg |
| Calcium | 180 mg (9.0 mEq) | 180 mg (9.0 mEq) | 180 mg (9.0 mEq) |
| Phosphorus | 100 mg | 100 mg | 100 mg |
| Magnesium | 12.0 mg | 12.0 mg | 12.0 mg |
| Iron | 1.8 mg | 1.8 mg | 1.8 mg |
| Zinc | 1.50 mcg | 1.50 mcg | 1.50 mcg |
| Manganese | 12 mcg | 12 mcg | 12 mcg |
| Copper | 250 mcg | 250 mcg | 250 mcg |
| Iodine | 6 mcg | 6 mcg | 6 mcg |
| Selenium | 1.8 mcg | 1.8 mcg | 1.8 mcg |
| Sodium | 43 mg (1.9 mEq) | 43 mg (1.9 mEq) | 43 mg (1.9 mEq) |
| Potassium | 129 mg (3.3 mEq) | 129 mg (3.3 mEq) | 129 mg (3.3 mEq) |
| Chloride | 81 mg (2.3 mEq) | 81 mg (2.3 mEq) | 81 mg (2.3 mEq) |
| Total Lutein (mcg/liter as fed) | 150 | 300 | 1150 |
| Total DHA (mg/liter as fed) | 112 | 112 | 115 |
| Ratio - Lutein (mcg):DHA (mg) as fed | 1.3:1 | 3:1 | 10:1 |

The exemplified ready-to-feed formulas (caloric density of 812 kcal/liter) are administered to preterm infants to provide from 7-300 mcg/kg of lutein per day. The administered formula improves eye health as described herein, and are especially useful as applied to preterm infants to reduce the risk of retinopathy of prematurity and helps protect the eyes from natural or artificial light, especially biliary lights.

Experiment

A study is conducted to compare plasma lutein concentrations in breastfed infants with plasma lutein concentrations in formula fed infants. The latter received one of three formulas defined by lutein concentrations of 32.6 mcg/liter (L1), 52.6 mcg/liter (L2), or 14.6 mcg/liter (CTRL). The study groups and resulting plasma lutein concentrations are summarized in the following table.

| Feeding Group | Plasma Lutein (mcg/dL) [‡] | |
|---|---|---|
| | Study Day 1 | Study Day 56 |
| Control (CTRL) - no added lutein Total inherent lutein 14.6 mcg/liter lutein) | 1.37 ± 0.29 [a] (0.40-5.10) 20 | 2.17 ± 0.12 [a] (1.16-3.25) 18 |
| Formula L1 Added lutein approximately 1 8 mcg/liter Inherent lutein approximately 14.6 mcg/liter Total lutein 32.6 mcg/L | 0.78 ± 0.09 [a] (0.27-2.09) 24 | 2.21 ± 0.16 [a] (0.20-3.61) 22 |
| Formula L2 Added lutein approximately 38mcg/liter Inherent lutein approximately 14.6 mcg/liter Total lutein 52.6 mcg/L | 0.97 ± 0.13 [a] (0.20-2.31) 21 | 3.25 ± 0.26 [b] (0.60-4.70) 19 |
| Human Milk (HM) 6.5-107.8 mcg/liter lutein | 6.53 ± 0.54 [b] (1.69-14.12) 24 | 5.88 ± 0.77 [c] (0.49-20.09) 26 |

[‡]Values are presented as mean ± SEM, (range) n Values in a column with superscripts without a common letter differ(p<0.05). See text for actual p values. Statistical comparisons among the formula groups are done using the Kruskal-Wallis test. Comparisons between the formula groups and the human milk group are done using the Wilcoxon rank-sum test.

Plasma lutein concentrations (at day 56 of the study) are used as the primary variable in the study. The primary comparison is the difference in plasma lutein concentrations between the L2 and CTRL formula groups. Secondary comparisons included differences in plasma lutein concentrations among the formula groups (CTRL, L1, L2) and differences between the formula groups and the human milk group. Plasma lutein concentrations on day 56 from a total of 85 infants (CTRL, n=18; L1, n=22; L2, n=19; HM, n=26) is used in these analyses and results reported as mean±SEM in the following table.

Infants in the L2 formula group have significantly higher (p<0.05) plasma concentrations of lutein than infants in the L1 and CTRL formula groups. Plasma lutein are not different between the L1 and CTRL formula groups. The human milk group has higher plasma lutein concentrations than the CTRL (p<0.0001), L1 (p<0.0001), and L2 (p=0.0052) formula groups. Plasma lutein concentration is significantly correlated with lutein intake (r=0.436, p=0.0014). Lutein intake and plasma response from the study are also summarized in FIG. 1.

The data from the study show that lutein is surprisingly less bioavailable from infant formula than from human milk (see FIG. 1). As such, in order for an infant formula to produce plasma lutein concentrations in infants similar to that produced by feeding human milk, an infant formula must be formulated to contain at least about 50 mcg/liter of lutein, preferably from 100 mcg/liter to about 200 mcg/liter.

What is claimed is:

1. An infant formula comprising fat, protein, carbohydrate, vitamins, and minerals, including docosahexaenoic acid and, on a ready-to-feed basis, at least about 75 mcg/liter of lutein, wherein the weight ratio of lutein (mcg) to docosahexaenoic acid (mg) is from about 1:2 to about 10:1 and the formula is free of egg phospholipids.

2. The infant formula of claim 1 wherein the formula comprises from about 75 to about 230 mcg/liter of lutein.

3. The infant formula of claim 1 wherein the formula comprises from about 100 to about 200 mcg/liter of lutein.

4. The infant formula of claim 1 wherein the weight ratio of lutein (mcg) to docosahexaenoic acid (mg) is from about 1.5:1 to about 10:1.

5. The infant formula of claim 1 wherein the weight ratio of lutein (mcg) to docosahexaenoic acid (mg) is from about 2:1 to about 5:1.

6. The infant formula of claim 1 wherein the formula has a caloric density of from 20 to 30 kcal/fluid ounce.

7. The infant formula of claim 1 wherein the formula comprises a combination of free lutein and zeaxanthin from a single source, that source being a crystalline extract of *Tagetes erecta* in which the free lutein represents from 85% to 95% by weight of the combination and the free zeaxanthin represents from about 5% to about 15% by weight of the combination.

8. The infant formula of claim 1 wherein the formula is a powder.

9. The infant formula of claim 1 wherein the formula is a liquid.

10. The infant formula of claim 1 wherein the lutein comprises at least 25% by weight of added lutein.

11. A method to reduce the risk of retinopathy of prematurity in preterm infants, said method comprising administering to a preterm infant in need thereof a formula according to claim 1 to provide the infant from about 7 to about 300 mcg/kg/day of lutein.

12. A method to promote retinal health and vision development in infants, said method comprising administering to an infant in need thereof a formula according to claim 1 to provide the infant from about 14 to about 220 mcg/kg/day of lutein.

13. A method to reduce the risk of retinopathy of prematurity in preterm infants, said method comprising administering to a preterm infant in need thereof a formula according to claim 1 to provide the infant from about 14 to about 220 mcg/kg/day of lutein.

14. A method to promote retinal health and vision development in infants, said method comprising administering to an infant in need thereof a formula according to claim 1 to provide the infant from about 7 to about 300 mcg/kg/day of lutein.

15. An infant formula comprising, on a ready-to-feed basis,
   (a) from about 54 to about 108 gm/liter of carbohydrate,
   (b) from about 20 to about 54 gm/liter of fat,
   (c) from about 7 to about 24 gm/liter of protein,
   (d) from about 100 to about 200 mcg/liter of lutein, and
   (e) docosahexaenoic acid,
   wherein the weight ratio of lutein (mcg) to docosahexaenoic acid (mg) is from about 2:1 to about 5:1 and the formula is free of egg phospholipids.

16. The infant formula of claim 15 wherein the formula comprises a combination of free lutein and zeaxanthin from a single source, that source being a crystalline extract of *Tagetes erecta* in which the free lutein represents from 85% to 95% by weight of the combination and the free zeaxanthin represents from about 5% to about 15% by weight of the combination.

17. An infant formula comprising fat, protein, carbohydrate, vitamins, and minerals, including docosahexaenoic acid and, on a ready-to-feed basis, from about 75 mcg/liter of lutein to about 1150 mcg/liter of lutein, wherein the weight ratio of lutein (mcg) to docosahexaenoic acid (mg) is from about 1:2 to about 10:1 and the formula is free of egg phospholipids.

* * * * *